US007968843B2

United States Patent
Nishiyama

(10) Patent No.: US 7,968,843 B2
(45) Date of Patent: *Jun. 28, 2011

(54) METHOD AND APPARATUS FOR SIMULTANEOUS SEM AND OPTICAL EXAMINATION

(75) Inventor: Hidetoshi Nishiyama, Tokyo (JP)

(73) Assignee: JEOL Ltd., Tokyo (JP)

( * ) Notice: Subject to any disclaimer, the term of this patent is extended or adjusted under 35 U.S.C. 154(b) by 331 days.

This patent is subject to a terminal disclaimer.

(21) Appl. No.: 12/349,195

(22) Filed: Jan. 6, 2009

(65) Prior Publication Data
US 2009/0256074 A1    Oct. 15, 2009

(30) Foreign Application Priority Data
Apr. 10, 2008   (JP) .................................. 2008-101990

(51) Int. Cl.
*H01J 37/26*    (2006.01)
(52) U.S. Cl. ......................... 250/306; 250/307; 430/296
(58) Field of Classification Search .................. 250/306, 250/307, 309, 310, 311; 430/296
See application file for complete search history.

(56) References Cited

U.S. PATENT DOCUMENTS

| | | | | |
|---|---|---|---|---|
| 2004/0114120 A1* | 6/2004 | Van De Kerhof et al. | ...... | 355/67 |
| 2005/0173632 A1* | 8/2005 | Behar et al. | ...... | 250/311 |
| 2005/0184233 A1* | 8/2005 | Park et al. | ...... | 250/307 |
| 2008/0308731 A1* | 12/2008 | Nishiyama et al. | ...... | 250/310 |

FOREIGN PATENT DOCUMENTS

| JP | 06-318445 A | 11/1994 |
|---|---|---|
| JP | 2007-292702 A | 11/2007 |

OTHER PUBLICATIONS

Green, Evan Drake Harriman, Ph.D., Chapter 1, Introduction, Atmospheric scanning electron microscopy, Stanford University, 1993, pp. 1-12.

* cited by examiner

*Primary Examiner* — Phillip A Johnston
*Assistant Examiner* — Nicole Ippolito Rausch
(74) *Attorney, Agent, or Firm* — The Webb Law Firm

(57) ABSTRACT

Method and apparatus capable of observing a liquid sample. An optical image of the sample and an image using a primary beam, such as an electron beam or charged-particle beam, can be obtained at the same time. The apparatus has a film including a first surface on which the liquid sample is held. The primary beam irradiation column and optical image acquisition viewer are located on opposite sides of the film that acts to block light.

19 Claims, 4 Drawing Sheets

METHOD AND APPARATUS FOR SIMULTANEOUS SEM AND OPTICAL EXAMINATION

BACKGROUND OF THE INVENTION

1. Field of the Invention

The present invention relates to an apparatus and method capable of inspecting a specimen held on a film by irradiating the specimen with a primary beam, such as a charged-particle beam. More particularly, where the specimen consists of biological cells, the invention relates to observation and inspection of reactions of the cells when a stimulus is given to them.

2. Description of Related Art

In the fields of life science and pharmaceutics, it is important to observe reactions of biological cells produced by giving a stimulus (such as electricity, chemical substance, or medicine) to them. In the past, optical microscopes have been used for such observation. Frequently, important portions to be observed are very tiny regions of less than 0.1 µm that are impossible to observe with an optical microscope. For example, diseases arising from inability to exchange information-carrying substances normally among biological cells include hypertension, diabetes insipidus, arrhythmia, myopathy, diabetes, and deprementia. Exchange of substances among cells is performed by membrane protein molecules (such as receptors or ion channels) having sizes of about 10 nm and existing in cell membranes. Because it is difficult to observe such membrane protein molecules with optical microscopes, there has been a demand for a technique enabling observation using a scanning electron microscope (SEM) having high resolution.

However, a sample containing a specimen to be inspected with an inspection apparatus incorporating SEM capabilities is normally placed in a sample chamber whose inside pressure has been reduced by vacuum pumping. The sample placed in the sample chamber, which, in turn, is placed in a reduced-pressure ambient in this way, is irradiated with an electron beam (charged-particle beam). Secondary signals, such as secondary electrons or backscattered electrons, produced from the sample in response to the irradiation are detected. In such inspection of a sample using SEM, the sample is exposed to a reduced-pressure ambient. Therefore, moisture evaporates from the sample, so that the cells die. It has then been impossible to observe reactions to a stimulus.

Accordingly, when an inspection is performed under the condition where the sample contains moisture, it is necessary to prevent the sample from being exposed to the reduced-pressure ambient; otherwise, moisture would evaporate from the sample. One conceivable method of inspecting a sample using SEM without exposing the sample to a reduced-pressure ambient in this way consists of preparing a sample holder whose opening (aperture) for transmission of charged particles has been sealed off by a film, placing the sample in the holder, and installing the holder in an SEM sample chamber that is placed in the reduced-pressure ambient.

The inside of the sample holder in which the sample is placed is not evacuated. The film that covers the opening formed in the sample holder can withstand the pressure difference between the reduced-pressure ambient inside the SEM sample chamber and the ambient (e.g., atmospheric-pressure ambient) of the inside of the sample holder that is not pumped down. Furthermore, the film permits an electron beam to pass therethrough (see JP-T-2004-515049).

When a sample is inspected, an electron beam is directed at the sample placed within the sample holder from outside the holder via the film on the holder placed in the SEM sample chamber that is in a reduced-pressure ambient. Backscattered electrons are produced from the irradiated sample. The backscattered electrons pass through the film on the sample holder and are detected by a backscattered electron detector mounted in the SEM sample chamber. Consequently, an SEM image is derived. However, with this technique, the sample is sealed in the closed space and so it has been impossible to give a stimulus to cells from outside the sample holder, for example, using a manipulator.

An example of a method of obtaining an SEM image by preparing a film withstanding the pressure difference between vacuum and atmospheric pressure, irradiating a sample with an electron beam via the film, and detecting backscattered electrons produced from the sample in this way is described also in ""Atmospheric Scanning Electron Microscopy"", Green, Evan Drake Harriman, Ph.D., Stanford University, 1993 (especially, Chapter 1: Introduction).

Examples in which two films of the structure described above are placed opposite to each other with a sample interposed between the films and in which an image is acquired by a transmission electron microscope are described in JP-A-47-24961 and JP-A-6-318445. Especially, JP-A-47-24961 also states a case in which an SEM image of the sample interposed between such films is acquired.

JP-A-2007-292702 discloses a sample inspection apparatus equipped with an open-close valve for partitioning the space between a film and primary beam irradiation means within a vacuum chamber in order to permit the sample held on the film to be exchanged quickly and to prevent contamination inside the vacuum chamber.

Morphological variations induced by the aforementioned reactions of cells to which a stimulus has been given take place in very tiny areas and so it is impossible to observe the variations with an optical microscope. Hence, SEM imaging is essential. In order to observe cells by SEM while maintaining the liquid, a sample containing the cells has been sealed in a sample holder. An electron beam has been directed at the sample via a film formed on the sample holder, thus imaging the cells.

However, the sample holder is a narrow closed space. Therefore, it has been impossible to give a stimulus to cells present within a sealed sample holder using a manipulator (i.e., manipulation).

Even if a stimulus is given to cells that are not yet sealed in by some method or other, a sequence of operations that takes several minutes or more to perform needs to be carried out. The sequence of operations consists of hermetically sealing the sample holder, putting the holder into an SEM sample chamber, pumping down the sample chamber, and irradiating the holder with an electron beam. For this reason, it has been impossible to observe cells by SEM immediately after a stimulus is given to them.

In addition, it normally takes a time of 10 seconds to 100 seconds to capture an SEM image. Consequently, it has been difficult to identify a cell portion that undergoes a morphological variation in a few seconds. Therefore, where cells respond at high speeds to a stimulus, there is the problem that SEM imaging cannot be completed.

SUMMARY OF THE INVENTION

It is an object of the present invention to provide an inspection apparatus and method capable of obtaining high-resolution images of a specimen by giving a stimulus to the specimen held on a film, observing behavior of the specimen with an optical microscope, and simultaneously irradiating the specimen with a primary beam, such as a charged-particle beam via the film.

An inspection apparatus, according to the present invention, has: a primary beam irradiation column for irradiating a specimen to be inspected with a primary beam via a film; a signal detector for detecting a secondary signal produced from the specimen in response to the primary beam irradiation; and an optical image acquisition viewer for obtaining an optical image of the specimen by illuminating the specimen with light. In one feature of this inspection apparatus, the film acts to block the light. The primary beam irradiation column and the optical image acquisition viewer are located on opposite sides of the film.

Another inspection apparatus, according to the present invention, has: a film having a first surface on which a specimen to be inspected is held; a vacuum chamber for reducing the pressure of an ambient in contact with a second surface of the film; a primary beam irradiation column connected with the vacuum chamber and directing a primary beam at the specimen via the film; a signal detector for detecting a secondary signal produced from the specimen in response to the primary beam irradiation; and optical image acquisition viewer for obtaining an optical image of the specimen by illuminating the specimen with light. In one feature of this inspection apparatus, the film acts to block the light. The primary beam irradiation column and the optical image acquisition viewer are located on opposite sides of the film.

If the first surface of the film is made open to permit access to the specimen from the outside, a stimulus can be given to the specimen using a manipulator or the like. The resulting reaction of the specimen can be observed or inspected. This offers convenience.

If the first surface of the film is the upper surface of the film and the second surface of the film is the lower surface of the film, a sample containing the specimen can be stably placed on the first surface of the film, thus offering convenience.

An inspection method, according to the present invention, comprises the steps of: holding a specimen to be inspected onto a first surface of a film; irradiating the specimen with a primary beam via the film from a side of a second surface of the film; detecting a secondary signal produced from the specimen in response to the primary beam irradiation; and illuminating the specimen with light from a side of the first surface of the film and obtaining an optical image of the specimen.

In one feature of this method, the film acts to block the light.

Another inspection method, according to the present invention, comprises the steps of: holding a specimen to be inspected onto a first surface of a film; reducing the pressure of an ambient in contact with a second surface of the film; irradiating the specimen with a primary beam via the film from a side of the ambient in contact with the second surface of the film; detecting a secondary signal produced from the specimen in response to the primary beam irradiation; and illuminating the specimen with light from a side of the first surface of the film and obtaining an optical image of the specimen. In one feature of this method, the film acts to block the light.

In the above-described inspection methods, if the first surface of the film is made open to permit access to the specimen from the outside, a stimulus can be given to the specimen using a manipulator or the like. The resulting reaction of the specimen can be observed or inspected, offering convenience.

If the first surface of the film is the upper surface of the film and the second surface of the film is the lower surface of the film, a sample containing the specimen can be stably placed on the first surface of the film, thus offering convenience.

In the present invention, the primary beam is directed at the specimen to be inspected by the primary irradiation column via the film. The resulting secondary signal from the specimen is detected by the signal detector. Light is directed at the specimen from a side opposite to the side where the primary irradiation column is located. An optical image of the specimen is obtained. The film acts to block the light.

Consequently, when the secondary signal from the specimen induced by the primary beam irradiation is detected by the signal detector simultaneously with the acquisition of the optical image, the light directed at the signal detector is blocked by the film.

Therefore, light that would normally produce noise when the secondary signal is detected does not enter the signal detector. Acquisition of the optical image and the detection of the secondary signal can be done simultaneously without problem.

As a result, while the specimen contained in the sample is being observed through the optical image, a high-resolution image of the specimen based on the secondary signal can be derived. In consequence, a stimulus can be given to the specimen cells using a manipulator or the like while checking the optical image. States of the cells obtained during and immediately after the application of the stimulus can be observed by SEM.

Other objects and features of the invention will appear in the course of the description thereof, which follows.

DESCRIPTION OF THE PREFERRED EMBODIMENTS

Inspection apparatus and methods, according to the present invention, are hereinafter described with reference to the drawings.

Figure 1:
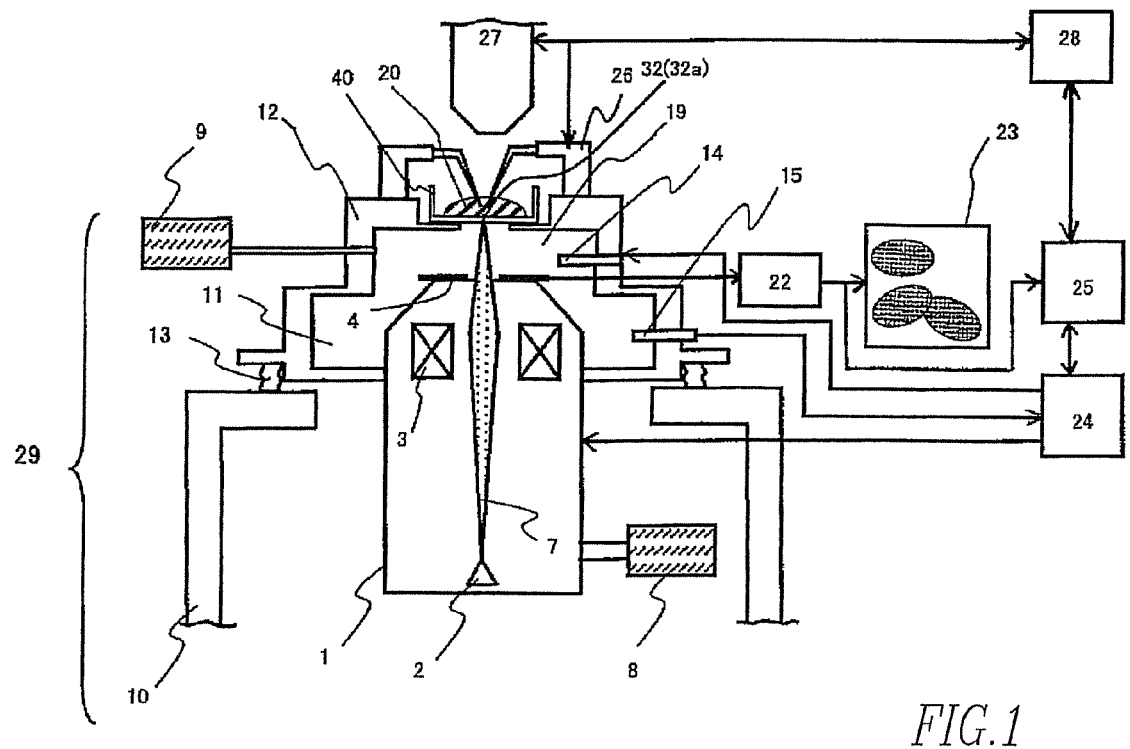
FIG. 1 is a schematic diagram of a sample inspection apparatus, according to the present invention, showing the configuration of the apparatus.

FIG. 1 is a schematic diagram of a sample inspection apparatus, according to the present invention. The apparatus consists chiefly of an optical microscope 27, a manipulator 26, and an electron beam apparatus section 29 located under a sample holder 40. The electron beam apparatus section 29 includes an electron optical column 1 forming a primary beam irradiation column. An electron gun 2 forming an electron source is disposed in the electron optical column 1 and emits an accelerated electron beam 7 that is a primary beam.

The electron beam 7 is one kind of charged-particle beam. The beam 7 is focused by a condenser lens (objective lens) 3.

The focused electron beam 7 is directed at a liquid sample 20 via a sample-holding film 32 (described later) formed on the sample holder 40. The liquid sample 20 is held on the sample holder 40. In the present embodiment, the liquid sample 20 includes biological cells to be inspected and a culture medium surrounding the cells.

The front-end side of the electron optical column 1 is connected with a vacuum chamber 11. The electron gun 2 is mounted in the base side of the column 1. The base side of the column 1 is located under the vacuum chamber 11. Because of this configuration, the electron beam 7 released from the electron gun 2 travels upward through the column 1, passes through the space inside the vacuum chamber 11 and through the sample-holding film 32, and reaches the liquid sample 20.

During the irradiation, the electron beam 7 is deflected by deflection column (not shown). Thus, the beam 7 scans the liquid sample 20. At this time, the cells contained in the liquid sample 20 are also scanned with the beam 7.

The electron optical column 1 forms the primary beam irradiation column in this way. In the present embodiment, the column is of the inverted type. A backscattered electron detector 4 is mounted on the front-end side of the column 1 inside the vacuum chamber 11. The backscattered electron detector 4 detects backscattered electrons produced when the cells included in the liquid sample 20 are irradiated with the electron beam 7. For example, a semiconductor detector using a PN junction or a scintillator detector using a YAG crystal is used as the backscattered electron detector 4.

In any case, these detectors amplify even light signals and so if the illuminating light emitted from the optical microscope 27 and impinging on the liquid sample 20 hits the backscattered electron detector 4, a background against the backscattered electron signal is created. Consequently, it is necessary to take care to prevent the illuminating light from hitting the backscattered electron detector 4. Accordingly, in the present invention, light blocking capabilities are imparted to the sample-holding protective film 32.

The output signal from the backscattered electron detector 4 is sent to an image formation device 22 disposed outside the vacuum chamber 11. The image formation device 22 creates image data based on the detector output signal. The image data becomes image data corresponding to the SEM image. The image data is fed to a display device 23, which, in turn, displays an image based on the incoming image data. The displayed image becomes an SEM image.

If necessary, the image data formed by the image formation device 22 is sent to a computer 25. The computer 25 image-processes the image data and makes decisions based on the result of the image processing.

The inside of the electron optical column 1 is pumped down to a desired pressure by vacuum pump 8. The inside of the vacuum chamber 11 is evacuated to a desired pressure by vacuum pump 9. The vacuum chamber 11 is placed over a pedestal 10 via a vibration-proofing device 13.

A sample holder placement portion 12 is formed on top of the vacuum chamber 11 and provided with a hole to permit the electron beam 7 to be directed at the sample-holding film 32. The sample holder 40 is placed on the placement portion 12 via an O-ring (not shown). Consequently, the sample holder 40 is withdrawably supported in the vacuum chamber 11.

Figure 2:
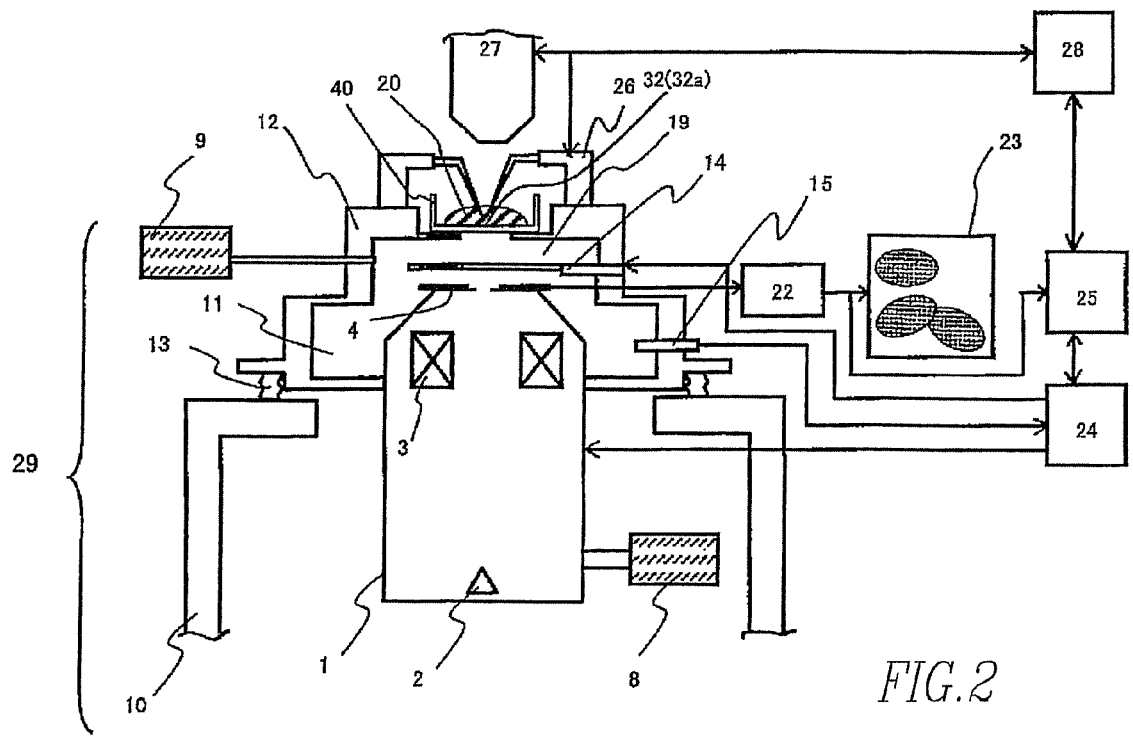
FIG. 2 is a schematic diagram similar to FIG. 1, but showing a different state.

A vacuum gauge 15 for detecting the pressure inside the vacuum chamber 11 is installed in the vacuum chamber 11. A shutter 14 that is in an open state in FIG. 1 is installed between the front end of the electron optical column 1 and the sample-holding film 32. When the sample-holding film 32 is destroyed and the vacuum gauge 15 has detected a given rise in the pressure, the shutter 14 is automatically moved and closed as shown in FIG. 2. For example, if the sample-holding film 32 is destroyed and the liquid sample 20 flows into the vacuum chamber 11, and if the pressure inside the vacuum chamber rises above 100 Pa, the shutter 14 is moved as shown in FIG. 2.

Consequently, the liquid sample 20 that has flowed into the vacuum chamber 11 can be blocked by the shutter 14. Hence, contamination of the electron microscope column 1 and backscattered electron detector 4 is prevented. Where the shutter 14 is fitted with a catch pan for receiving the liquid sample, it is possible to cope with inflow of a large amount of liquid sample.

The shutter 14 partitions the vacuum chamber 11 into two vertically separated spaces not completely, but partially. Therefore, the shutter 14 is simple in structure and can operate at high speed. In the present embodiment, the shutter can be activated (i.e., a transition from the state of FIG. 1 to the state of FIG. 2 can be made) in 0.1 second after the vacuum gauge 15 detects a pressure rise. Furthermore, the shutter can be made thin. Consequently, the distance between the front end of the electron microscope column 1 and the sample-holding film 32 (i.e., the working distance of the SEM) can be reduced. Thus, high resolution can be accomplished.

The electron beam apparatus section 29 equipped with the electron optical column 1, vacuum chamber 11, shutter 14, and vacuum gauge 15 is controlled by an electron beam controller 24. The manipulator 26 for giving a stimulus (such as a voltage, chemical substance, or medicine) to the cells and for moving them if necessary and an optical microscope 27 are placed on the sample holder placement portion 12. The optical microscope 27 permits one to observe the cells and to check the position of the manipulator 26. These components are controlled by an overall controller 28.

The optical axis of the optical microscope 27 is coincident with the optical axis of the electron beam 7. Alternatively, the center of field of view of the optical microscope 27 is coincident with the center of field of view of the SEM image. A region observed by the optical microscope can be made substantially coincident with the SEM image. The field of view of the SEM image and the field of view of the optical microscope 27 can be adjusted by manipulating the manipulator 26 or moving the sample holder placement portion 12 on which the sample holder 40 is placed by means of a moving mechanism (not shown).

The sample inspection apparatus, according to the present invention, has the electron beam apparatus section 29, manipulator 26, optical microscope 27, electron beam controller 24, overall controller 28, image formation device 22, and display device 23. These portions are connected with the computer 25. Information can be exchanged between these portions.

Figure 3:
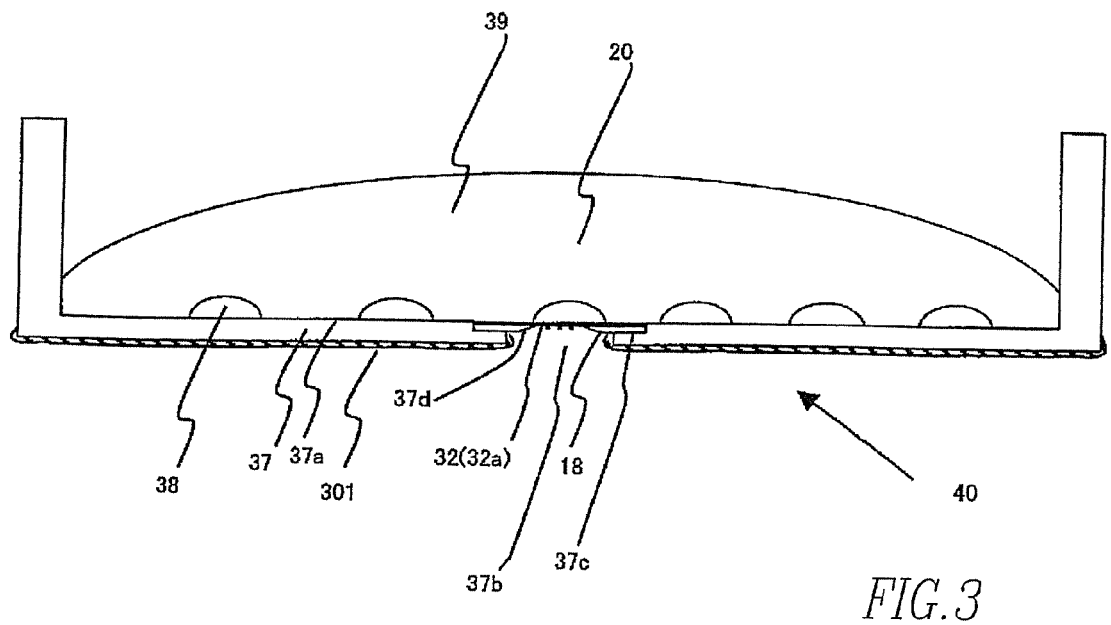
FIG. 3 is a cross-sectional view of a sample holder, according to the invention, showing the structure of the holder.

The sample holder 40 is constructed as shown in FIG. 3. The sample holder 40 is composed of a dish-like body portion 37 made of plastic or glass and a film holder (frame-like member) 18 on which the sample-holding film 32 is formed. The film 32 transmits the electron beam 7. The dish-like body portion 37 can have light-blocking capabilities to prevent the illuminating light from the optical microscope 27 from hitting the backscattered electron detector 4. A recessed portion is formed inside the dish-like body portion 37. The bottom surface of the recessed portion forms a sample-holding surface 37a that is open.

The sample-holding surface 37a of the dish-like body portion 37 is (centrally in the example of FIG. 3) provided with a through-hole 37b. A step portion 37c is formed around the hole 37b on the side of the sample-holding surface 37a. The film holder (frame-like member) 18 is disposed on the step portion 37c and has the sample-holding film 32. The sample-holding film 32 has a first surface 32a that forms the sample-holding surface 37a. The sample-holding surface 37a is substantially flush with the sample-holding surface 37a of the dish-like body portion 37. Consequently, at least a part of the sample-holding surface 37a of the sample holder 40 is formed by the sample-holding film 32.

Tapering portions 37d are formed on the side of the hole 37b on the opposite side of the sample-holding surface 37a. The tapering portions 37d are spread apart toward the surface on the opposite side of the sample-holding surface 37a. The spread angle is set to 90° to 120°.

A region of the lower surface of the sample holder 40 might be exposed to a vacuum ambient and become irradiated with the electron beam 7. A conductive film 301 is formed on this region to prevent charging of the sample holder 40 when it is irradiated with the beam 7. The conductive film 301 is in contact with the film holder 18 (frame-like member). Electric charge accumulated by being irradiated with the electron beam 7 can be dissipated away to the liquid sample 20 via the film holder (frame-like member) 18 made of silicon. The presence of the conductive film 301 reduces the charging of the lower surface of the sample holder 40 and can prevent displacement of the orbit of the beam 7 (that would normally be produced when the liquid sample 20 is irradiated with the beam 7) and distortion and illumination spots in the SEM image that would be normally produced by displacement of the orbit of backscattered electrons.

Accumulation of electric charge can be prevented with certainty by connecting a grounding line to the liquid sample 20 or electrically connecting the conductive film 301 with the sample holder placement portion 12. The conductive film 301 can be formed, for example, by vapor-depositing aluminum or gold or applying silver paste. The conductive film 301 acts also to prevent the illuminating light of the optical microscope from hitting the backscattered electron detector.

Figure 4:
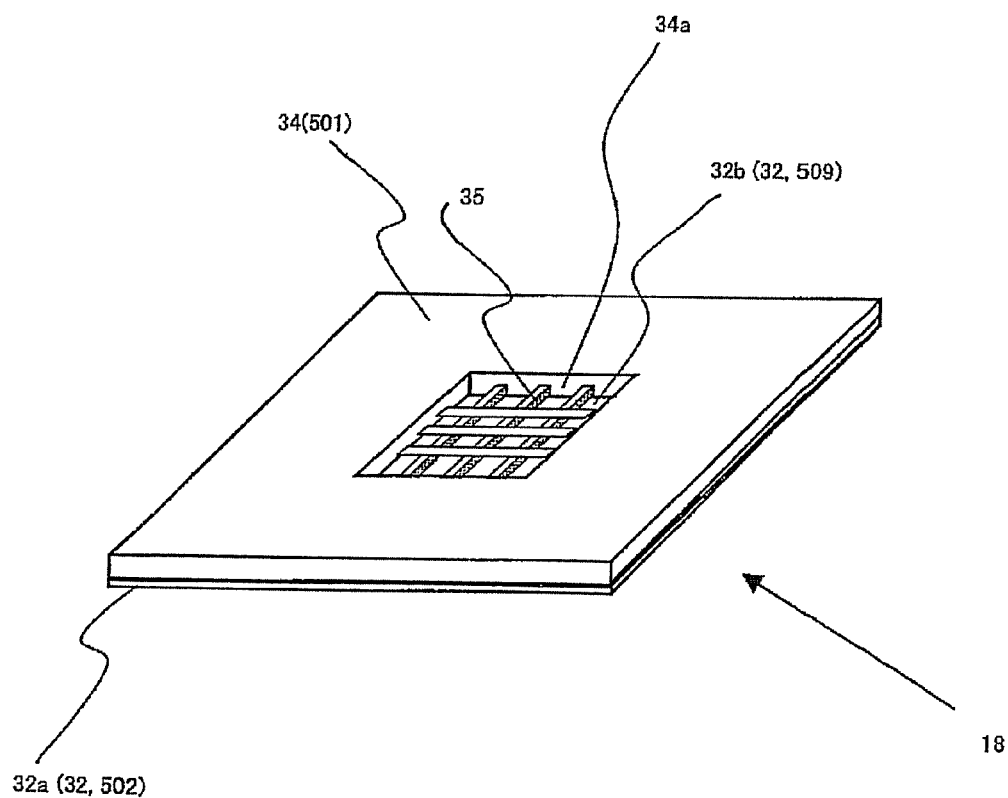
FIG. 4 is a schematic perspective view of a frame-like member constituting a sample holder, according to the present invention.

The structure of the film holder (frame-like member) 18 is shown in FIG. 4. The sample-holding film 32 is formed on a silicon substrate 34. A first surface 32a of the sample-holding film 32 (lower surface as viewed in FIG. 4; upper surface as viewed in FIG. 3) is exposed. The liquid sample 20 containing a liquid such as a culture medium and a specimen to be inspected such as cells is placed on the first surface (sample-holding surface) 32a of the sample-holding film 32. Since the first surface 32a is under atmospheric pressure, evaporation of moisture from the liquid sample 20 can be suppressed to a minimum.

The silicon substrate 34 is centrally provided with an opening 34a (upper surface in FIG. 4; lower surface in FIGS. 1 and 3) covered with the sample-holding film 32. A central portion of the second surface 32b of the sample-holding film 32 is exposed to the inside ambient of the vacuum chamber 11 through the opening 34a. The first surface 32a of the sample-holding film 32 is exposed to the atmospheric-pressure ambient, while the second surface 32b is exposed to the vacuum ambient. In order to withstand the pressure difference, the film 32 is supported and reinforced with a lattice 35.

Figure 5:
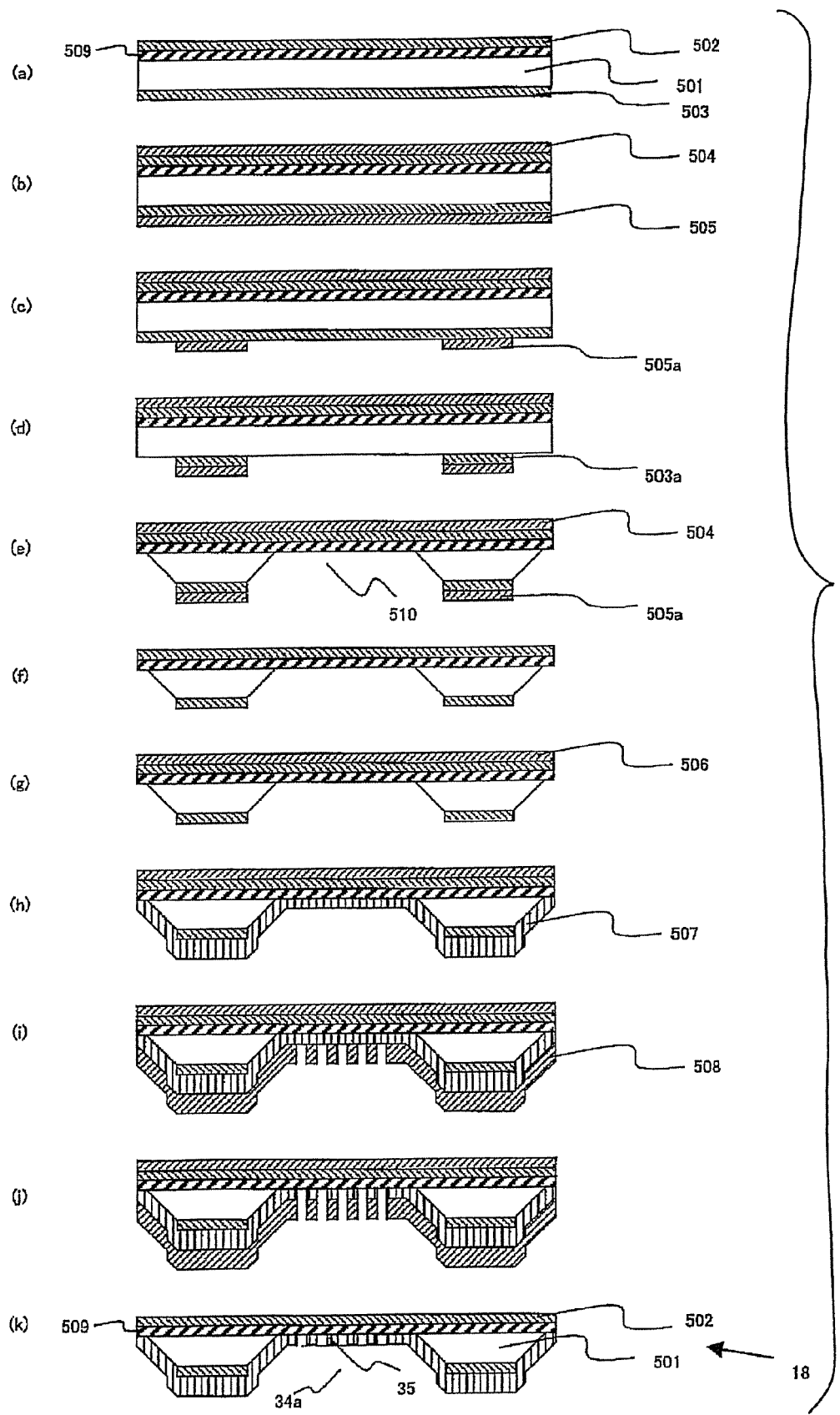
FIG. 5 shows cross sections illustrating a method of fabricating the frame-like member constituting the sample holder, according to the present invention.

A method of creating the film holder (frame-like member) 18 is next described by referring to FIG. 5. First, as shown FIG. 5(a), a film of Al 509 is formed on a silicon substrate 501 using sputtering or vacuum vapor deposition. Then, silicon nitride films 502 and 503 are formed using CVD (chemical vapor deposition). A typical thickness of the Al film 509 is 30 nm. A typical thickness of the silicon nitride film 502 is 30 nm. Layers of resist 504 and 505 are applied on the silicon nitride films 502 and 503, respectively (FIG. 5(b)). The layer of resist 505 is patterned photolithographically to leave behind resist layer portions 505a (FIG. 5(c)). Using the resist pattern as a mask, the silicon nitride film 503 is processed by dry etching, and silicon nitride film portions 503a are left behind (FIG. 5(d)).

Using the pattern as a mask, the silicon substrate 501 is wet-etched with KOH to form an opening 510 (FIG. 5(e)). The resist layer portions 504 and 505a are removed by ashing (FIG. 5(f)). Where the lattice 35 is not present, the film holder (frame-like member) 18 is completed at this point. Resist 506 is applied on the layer of silicon nitride film 502 (FIG. 5(g)). A layer of metal 507 of Al or Ni is formed to a thickness of 1 µm on the opposite side of the silicon nitride film 502 (FIG. 5(h)). Resist 508 is applied on the metal layer 507, and a pattern is photolithographically formed using a mask (FIG. 5(i)). Using the resist layer 508 as a mask, the metal layer 507 is etched (FIG. 5(j)). Finally, the resist layer 508 is removed by ashing or organic cleaning (FIG. 5(k)). As a result, the opening 34a and lattice 35 are formed.

The film holder (frame-like member) 18 fabricated in this way is inverted up and down from the state of FIG. 4. The first surface 32a (silicon nitride film 502) of the sample-holding film 32 composed of the Al film 509 and silicon nitride film 502 is taken as an upper surface. The second surface 32b (Al film 509) can also be taken as an upper surface.

Where the liquid sample 20 contains living cells, if the film in contact with the cells is a metal, metal ions may adversely affect the cells. In this case, it is important that the surface in contact with the cells be nonmetallic. Because the sample-holding film 32 contains the metallic film of Al, light can be blocked. Consequently, the illuminating light used in the optical microscope does not hit the backscattered electron detector 4. As a result, the backscattered electron image of the sample containing cells is free from a background signal due to the illuminating light.

The film holder (frame-like member) 18 is firmly attached to the step portion 37c over the hole 37b formed in the dish-like body portion 37 forming the sample holder 40. Thus, the sample holder 40 is fabricated (FIG. 3). To attach the holder (frame-like member) 18 to the step portion, bonding using an epoxy-based or silicone-based adhesive or fusion making use of heat, ultrasonic waves, or a laser beam can be used. Consequently, the film holder (frame-like member) 18 is firmly held in a position corresponding to the hole 37b in the sample-holding surface 37a of the body portion 37.

In the present embodiment, the dish-like body portion 37 and film holder (frame-like member) 18 are combined to fabricate the sample holder 40. The sample-holding film 32 may be directly firmly bonded to the body portion 37. The dish-like body portion 37 and the sample-holding film 32 may be fabricated integrally. Furthermore, cell adhesion molecules (described later) acting as molecules for bonding the sample may be applied to the sample-holding surface 37a including the first surface 32a of the sample-holding film 32.

The total thickness of the silicon nitride film 502 and Al film 509 is set within a range of from 20 to 1,000 nm. The thickness of the Al film 509 is set to 10 to 100 nm to block light. The sample-holding film 32 of the film holder (frame-like member) 18 is made of silicon nitride. In addition, the film 32 may be made of silicon oxide, boron nitride, polymer, polyethylene, polyimide, polypropylene, or carbon. Even where films of these materials are used, their film thicknesses are set within a range of from 10 to 1,000 nm. The film 509 may be made of Be or Mg instead of Al. In order to prevent scattering of the electron beam, it is desired that the material have a low atomic number.

The sample-holding film 32 made of the aforementioned material transmits the electron beam 7 but does not transmit gas or liquid. Moreover, it is necessary that the film be capable of withstanding a pressure difference of at least 1 atmosphere across the opposite surfaces. As the thickness of the sample-holding film 32 is reduced, scattering of the electron beam 7 is reduced and, therefore, the resolution is improved but the film is more easily damaged. As the thickness is increased, scattering of the electron beam 7 increases, resulting in decreased resolution. However, the film is less likely to be damaged. The preferable thickness of the film is 20 to 200 nm.

An inspection method, according to the present invention, is next described. First, as shown in FIG. 3, cells 38 to be inspected are cultured within a culture medium 39 using the sample holder 40. In order to culture the sample cells 38 in this way, it is necessary to graft the cells from the laboratory dish where they have been previously cultured to the sample holder 40. For this purpose, a normal method as described below is used.

The culture medium is Product No. D5796 of Sigma-Aldrich Co., for example. First, the culture medium is discarded from the laboratory dish where the cells have been previously cultured. A mixture liquid of trypsin and EDTA (ethylenediaminetetraacetic acid) is put into the dish to peel off the cells adsorbed to the dish. The peeled cells are then recovered into a centrifuge tube, and a culture medium is added. The trypsin is inactivated and then the cells are spun down. Then, the supernatant fluid is discarded from the centrifuge tube and the remaining liquid is stirred in the culture medium. A part (e.g., 1/10) of the stirred liquid including the cells 38 is entered into the sample holder 40. More culture medium 39 (reagent solution) is added.

Under this condition, the holder is allowed to stand still in a cell culture chamber. After a lapse of several hours, the cells 38 begin to be adsorbed onto the sample-holding surface 37a of the sample holder 40 including the first surface 32a of the sample-holding film 32 and proliferate. The aforementioned method may be modified according to cells and is merely shown as one example. Consequently, the cells 38 to be observed or inspected are cultured within the sample holder 40. It follows that the liquid sample 20 containing the cultured cells 38 and culture medium 39 is constituted.

Depending on biological cells, if cell adhesion molecules are applied to the sample-holding surface 37a of the sample holder 40 (especially, the first surface 32a (sample-holding surface) of the sample-holding film 32 observed with an electron beam), cultivation is facilitated. The cell adhesion molecules cause cells arranged for cultivation and cells proliferated by cultivation to be adsorbed onto the sample-holding surface. Examples of the cell adhesion molecules include collagen, fibronectin, vitronectin, cadherin, integrin, claudins, desmogleins, neuroligin, neurexin, selectin, laminins, and poly-L-lysine.

After the cells are cultured within the sample holder 40 as described above, the sample holder 40 is placed on the holder placement portion 12. At this time, the shutter 14 is closed and in the state of FIG. 2. Then, the insides of the vacuum chamber 11 and electron optical column 1 are pumped down to desired degrees of vacuum using pumps 8 and 9. For example, the pressure inside the vacuum chamber 11 is set to about 1 Pa. The pressure inside the electron optical column 1 (especially, around the electron gun 2) is set to about $10^{-4}$ to $10^{-5}$ Pa, for example.

Then, the positions of the cells 38 and of the manipulator 26 are checked with the optical microscope 27. A glass microtube holding microelectrodes therein is installed at the front end of the manipulator. A voltage can be applied to the cells through the microelectrodes. A liquid can be made to flow in and out through the glass microtube.

Under this condition, the manipulator 26 is moved while making an observation with the optical microscope 27 to bring the cells 38 close to the glass microtube. Then, a negative pressure is applied to the glass microtube to bring it into intimate contact with the cell membranes. As a result, potential response can be measured.

When the manipulator 26 is moved as described above, if the sample-holding film 32 is erroneously damaged and the liquid sample 20 enters the vacuum chamber 11, the sample 20 can be blocked by the shutter 14 because the shutter 14 is closed. Consequently, the contamination of the electron optical column 1 is prevented. Where the shutter 14 is not present, the liquid sample 20 enters the electron optical column 1. This makes it necessary to clean the apparatus. At times, the apparatus is made unusable.

We now return to the observation sequence. After checking that the sample-holding film 32 on which the liquid sample 20 is placed is not destroyed, the shutter 14 is opened.

Subsequently, an electrical stimulation is given to the cells 38 using the microelectrodes installed at the front end of the manipulator 26. The resulting reaction is observed with the optical microscope 27. These portions of the cells where a variation occurs are identified.

Then, as shown in FIG. 1, the electron beam 7 is directed at these portions of the liquid sample 20 including the cells 38 from the electron optical column 1 to perform imaging. The beam 7 passes through the sample-holding film 32 of the sample holder 40 and hits the cells 38. Backscattered electrons produced from the cells 38 in response to the irradiation are detected by the backscattered electron detector 4.

Since the aforementioned tapering portions 37d are formed around the hole 37b of the dish-like body portion 37 forming the sample holder 40, collision of the backscattered electrons against the inner side surface of the hole 37b can be suppressed to a minimum. That is, the backscattered electrons can be suppressed from being blocked. The backscattered electrons can be detected efficiently by the backscattered electron detector 4.

A detection signal produced from the backscattered electron detector 4 is fed to the image formation device 22, which, in turn, forms image data based on the detection signal. Based on the image data, an image (SEM image) is displayed on the display device 23. A high-resolution image that cannot be obtained with the optical microscope 27 can be derived.

Because the sample-holding film 32 contains the Al film 509, the light illuminating the sample from the optical microscope does not reach the backscattered electron detector present inside the vacuum chamber. Therefore, the sample can be imaged with the optical microscope and SEM simultaneously. In consequence, the behavior occurring immediately after a stimulus is given to the cells is observed with the optical microscope. Where a high-resolution image is required, SEM imaging can be done instantly. For this reason, it is possible to cope with a case where the reaction speed of the cells to the stimulus is high.

After the imaging, the shutter 14 is closed to prevent contamination of the electron optical column 1 if the sample-holding film 32 should be destroyed. Before a variation caused by application of a stimulus to the cells 38 is observed by SEM as described above, an observation may be made with the optical microscope 27. Also, at this time, if the shutter 14 is closed, risk of contamination occurring when the sample-holding film 32 is broken can be reduced. In any case, if the shutter 14 is closed when the electron beam 7 is not directed at the liquid sample 20, the probability of contamination of the inside of the apparatus can be reduced by shortening the interval for which the shutter 14 is opened during inspection.

Where the speed of reaction of the cells 38 to the stimulus is low, the shutter 14 may be once closed. The shutter 14 may be again opened at a time when a reaction is deemed to have taken place. Then, imaging may be performed using the electron beam 7. The reaction can be checked with the optical microscope 27.

Figure 6:
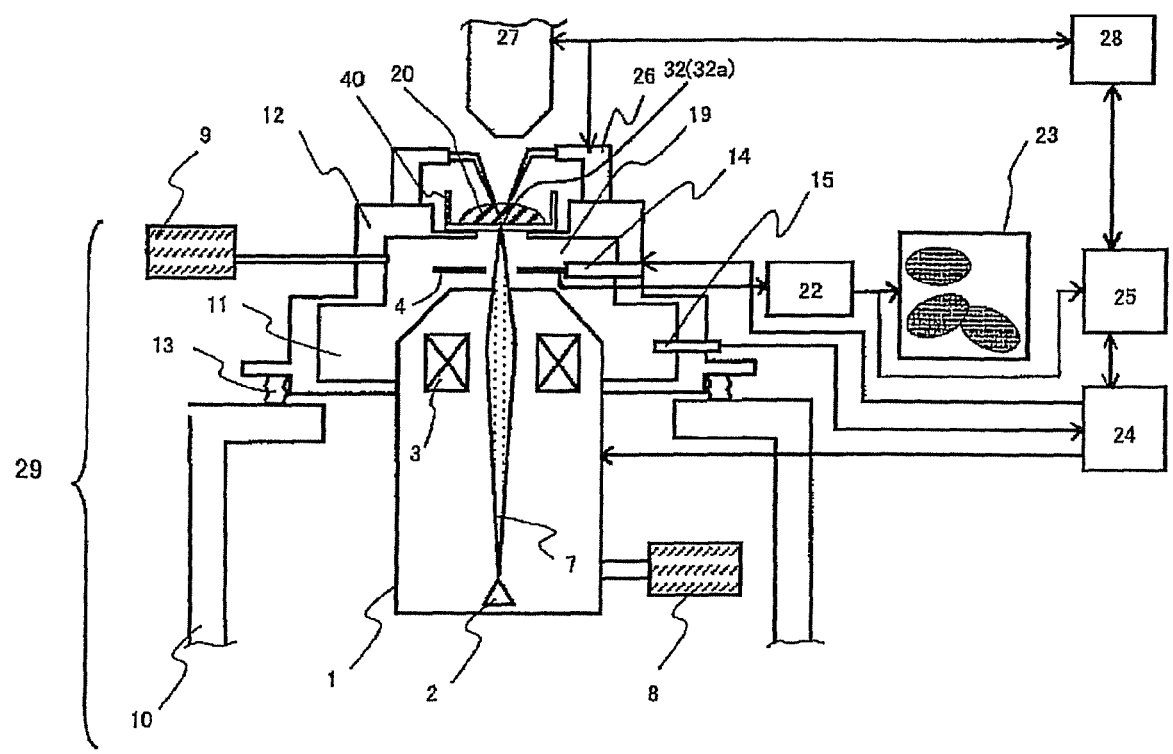
FIG. 6 is a schematic diagram of another sample inspection apparatus, according to the present invention, showing the configuration of the apparatus.

In the apparatus of the present embodiment, the shutter 14 and backscattered electron detector 4 are designed separately. They may also be fabricated integrally as shown in FIG. 6. That is, the backscattered electron detector 4 is mounted at the front end of the shutter 14. When the shutter 14 is open, the backscattered electron detector 4 is located immediately above the electron optical column 1. The efficiency at which backscattered electrons are detected is maximized.

The manipulator 26 can have a mechanism capable of spraying a chemical substance or medicine into the liquid sample 20. Behavior of the cells 38 in response to the chemical substance or medicine can be observed or inspected while observing the cells by SEM. Furthermore, a function of permitting a liquid to flow out can be imparted to the manipulator 26. This permits the sprayed substance to be recovered. Also, the pH of the culture medium and the osmotic pressure can be maintained constant.

In the foregoing, backscattered electrons are used to form an image. Backscattered electrons produce a signal intensity proportional to the atomic number. Therefore, where the specimen is almost totally made of substances of low atomic numbers, such as a biological specimen, the image contrast is very low, and it is difficult to improve the resolution.

Accordingly, a heavy metal, such as gold, may be adsorbed onto portions of the cells 38 to be noticed in their behavior. In particular, gold is adsorbed onto the portions (antigen) via an antibody by causing the antigen tagged with gold particles having the nature of being adsorbed on the portions (antigen) to be sprayed against the cells by making use of an antigen-antibody reaction. Furthermore, a fluorescent dye or quantum dots (e.g., nanoparticles of Si or particles of CdSe coated with ZnS and having sizes of 10 to 20 nm) that emit light when irradiated with an electron beam may be previously adsorbed onto certain portions of the cells 38, and the emitted light may be observed with an optical microscope.

In the above embodiment, normally used gold particles have particle diameters of 10 to 30 nm. However, the adsorptive force between the antibody and gold particles is weak, and gold particles of 10 to 30 nm may not be attached. In this case, very small gold particles (nanogold particles) having particle diameters of the order of nanometers are first attached to the antibody. Under this condition, the gold particles are too small and it is difficult to observe them by SEM. Silver is adsorbed around the gold particles by making use of a silver sensitizer. This makes it easier to detect them by SEM.

In the foregoing, cells previously cultured in a laboratory dish are taken out and grafted onto the sample holder 40. Then, the cells are cultured. Alternatively, cells may be taken from a living organism and directly placed on the sample-holding surface 37*a* of the sample holder 40. The cells may be cultured in the sample holder 40.

As described so far, use of the present invention makes it possible to observe or inspect a specimen via the sample-holding film 32, the specimen being contained in a liquid. Especially, the use of an open sample chamber facilitates giving a stimulus to cells because access to the sample including a specimen to be inspected can be made from the outside. Furthermore, the Al film 509 is formed on a part of the sample-holding film 32 to provide light-blocking capabilities. Illuminating light from the optical microscope 27 can be prevented from reaching the backscattered electron detector 4. Consequently, the liquid sample 20 can be imaged simultaneously by the optical microscope 27 and electron beam apparatus section (SEM) 29. Even where the response speed of the cells to a stimulus is high, variations in the cells can be observed with the optical microscope. Where a high-resolution image is required, SEM imaging can be done instantly.

Where the sample-holding film 32 is broken during observation using the SEM (the shutter 14 is open as shown in FIG. 1), the liquid sample 20 flows into the vacuum chamber 11, increasing the pressure. The pressure rise is detected by the vacuum gauge 15. If a pressure higher than 100 Pa, for example, is detected, the information is sent to the electron beam controller 24. An instruction for closing the shutter 14 is sent to the shutter 14. As a result, the shutter 14 is closed as shown in FIG. 2. The liquid sample 20 is blocked by the shutter 14. Where the amount of the sample 20 is large, it is possible to prepare a catch pan on the shutter 14. It takes only a short time of 0.1 second until the shutter 14 is closed after the pressure rise is detected. The contamination of the electron optical column 1 can be reduced to a level at which the column does not need to be cleaned.

In the above embodiments, an electron beam is used as the primary beam. If the sample-holding film 32 shows sufficient shock resistance and strength against impingement of another charged-particle beam, such as a helium ion beam, the invention can also be applied in a case where the other charged-particle beam is used.

In the above embodiments, backscattered electrons are used as a secondary signal. Information regarding the cells 38 to be-inspected can also be obtained by detecting other forms of information, such as secondary electrons, X-rays, cathodoluminescent light, and electric current absorbed into the cells 38. It is convenient to use the manipulator 26 in measuring the absorption current.

It is required that the sample-holding film 32 of the present embodiment withstand a pressure difference of at least 1 atm. and that gas or liquid do not flow in or out. Specifically, the material of the film 32 includes at least one of polymer, polyethylene, polyimide, polypropylene, carbon, silicon oxide, silicon nitride, and boron nitride together with the metal layer. The total film thickness is in a range of from 20 to 1,000 nm.

In this way, the inspection apparatus, according to the present invention, has the primary beam irradiation column 1 for irradiating the inspected sample cells 38 with the primary beam via the film 32, the signal detector 4 for detecting a secondary signal produced from the sample cells 38 in response to the primary beam irradiation, and the optical microscope 27 for obtaining an optical image of the sample cells 38 by illuminating the sample cells 38 with light. The film 32 acts to block the light. The primary beam irradiation column 1 and the optical microscope 27 are disposed on opposite sides of the film 32.

The inspection apparatus of the present invention has: the film 32 having the first surface 32*a* on which the sample cells 38 to be inspected is held; the vacuum chamber 11 for reducing the pressure in the ambient in contact with the second surface 32*b* of the film 32; the primary beam irradiation column 1 connected with the vacuum chamber 11 and irradiating the sample cells 38 with a primary beam via the film 32; the signal detector 4 for detecting a secondary signal produced from the sample cells 38 in response to the primary beam irradiation; and the optical microscope 27 for obtaining an optical image of the sample cells 38 by illuminating the sample cells 38 with light. The film 32 acts to block the light. The primary beam irradiation column 1 and the optical microscope 27 are disposed on opposite sides of the film 32.

The inspection method of the present invention is implemented by carrying out an inspection of a specimen by the use of the above-described inspection apparatus.

The inspection method of the present invention starts with causing the sample cells 38 to be inspected to be held on the first surface 32a of the film 32. The sample cells 38 are irradiated with a primary beam from a side of the second surface 32b of the film 32 via the film 32. A secondary signal produced from the sample cells 38 in response to the primary beam irradiation is detected. The sample cells 38 are illuminated with light from a side of the first surface 32a of the film 32, and an optical image of the sample cells 38 is obtained. The film 32 acts to block the light.

The inspection method of the present invention starts with causing the sample cells 38 to be inspected to be held on the first surface 32a of the film 32. The pressure of the ambient in contact with the second surface 32b of the film 32a is reduced. The sample cells 38 are irradiated with a primary beam from a side of the ambient in contact with the second surface 32b of the film 32 via the film. A secondary signal produced from the sample cells 38 in response to the primary beam irradiation is detected. The sample cells 38 are illuminated with light from a side of the first surface 32a of the film 32, and an optical image of the sample cells 38 is obtained. The film 32 acts to block the light.

In the above-described inspection apparatus and method, the first surface 32a of the film 32 on which the sample cells 38 are held is made open to permit access to the sample cells 38 from the outside using a manipulator or the like. At this time, the first surface 32a of the film 32 is the upper surface of the film 32, while the second surface 32b of the film 32 is the lower surface of the film 32.

The film 32 contains a metal layer and a layer made of at least one of polymer, polyethylene, polyimide, polypropylene, carbon, silicon oxide, silicon nitride, and boron nitride. The total thickness of these layers can be set within a range of from 20 to 1,000 nm.

In particular, the thickness of the metal layer can be set within a range of from 10 to 100 nm. The metal layer can be made of Be, Mg, or Al. The metal layer can be located not on a side of the first surface 32a of the film 32.

The primary beam can be an electron beam or a charged-particle beam. The secondary signal can be at least any one type of backscattered electrons, secondary electrons, absorption current, cathodoluminescent light, and X-rays.

Having thus described my invention with the detail and particularity required by the Patent Laws, what is desired protected by Letters Patent is set forth in the following claims.

The invention claimed is:

1. An inspection apparatus comprising:
   primary beam irradiation means for irradiating a specimen to be inspected with a primary beam via a film;
   signal detection means for detecting a secondary signal produced from the specimen in response to the primary beam irradiation and passed through the film; and
   optical image acquisition means for illuminating the specimen with light and obtaining a light reflected optical image of the specimen in response to the light illumination;
   wherein the film acts to block the light, and
   wherein the primary beam irradiation means and the optical image acquisition means are located on opposite sides of the film, and
   wherein the film acts to block the illumination light so as to prevent the illuminating light from hitting the signal detection means.

2. An inspection apparatus comprising:
   a film having a first surface on which a specimen to be inspected is held;
   a vacuum chamber for reducing the pressure of an ambient in contact with a second surface of the film;
   primary beam irradiation means connected with the vacuum chamber for irradiating the specimen with a primary beam via the film;
   signal detection means for detecting a secondary signal produced from the specimen in response to the primary beam irradiation and passed through the film; and
   optical image acquisition means for illuminating the specimen with light and obtaining a light reflected optical image of the specimen in response to the light illumination,
   wherein the primary beam irradiation means and the optical image acquisition means are located on opposite sides of the film and,
   wherein the film acts to block the illumination light so as to prevent the illuminating light from hitting the signal detection means.

3. An inspection apparatus as set forth in claim 1, wherein the first surface of said film on which the specimen is held is made open to permit access to the specimen from the outside.

4. An inspection apparatus as set forth in claim 1, wherein the first surface of said film is an upper surface of the film, while the second surface of the film is a lower surface of the film.

5. An inspection apparatus as set forth in claim 1 or 2, wherein said film contains a layer made of at least one of polymer, polyethylene, polyimide, polypropylene, carbon, silicon oxide, silicon nitride, and boron nitride and a metal layer, and wherein a total thickness of these layers is in a range of from 20 to 1,000 nm.

6. An inspection apparatus as set forth in claim 5, wherein said metal layer has a thickness of 10 to 100 nm.

7. An inspection apparatus as set forth in claim 5, wherein said metal layer is made of Be, Mg, or Al.

8. An inspection apparatus as set forth in claim 5, wherein said metal layer is not located on a side of the first surface of said film.

9. An inspection apparatus as set forth in claim 1 or 2, wherein said primary beam is an electron beam or a charged-particle beam, and wherein said secondary signal is at least any one type of backscattered electrons, secondary electrons, absorption current, cathodoluminescent light, and X-rays.

10. An inspection method for inspecting a specimen using an inspection apparatus as set forth in claim 1.

11. An inspection method comprising the steps of:
    preparing a film having a first surface and a second surface;
    holding a specimen to be inspected onto the first surface of the film;
    irradiating the specimen with a primary beam via the film from a side of the second surface of the film;
    detecting a secondary signal produced from the specimen in response to the primary beam irradiation and passed through the film; and
    illuminating the specimen with light from a side of the first surface of the film and obtaining a light reflected optical image of the specimen,
    wherein the film acts to block said illuminating light so as to prevent the illuminating light from interfering with the detection of the secondary signal.

12. An inspection method comprising the steps of:
preparing a film having a first surface and a second surface;
holding a specimen to be inspected onto the first surface of the film;
reducing the pressure of an ambient in contact with the second surface of the film;
irradiating the specimen with a primary beam via the film from a side of the ambient in contact with the second surface of the film;
detecting a secondary signal produced from the specimen in response to the primary beam irradiation and passed through the film; and
illuminating the specimen with light from a side of the first surface of the film and obtaining a light reflected optical image of the specimen,
wherein the film acts to block said illuminating light so as to prevent the illuminating light from interfering with the detection of the secondary signal.

13. An inspection method as set forth in claim 11 or 12, wherein the first film of said film on which the specimen is held is made open to permit access to the specimen from the outside.

14. An inspection method as set forth in claim 11 or 12, wherein the first surface of said film is an upper surface of the film, while the second surface of the film is a lower surface of the film.

15. An inspection method as set forth in claim 11 or 12, wherein said film contains a layer made of at least one of polymer, polyethylene, polyimide, polypropylene, carbon, silicon oxide, silicon nitride, and boron nitride and a metal layer, and wherein a total thickness of these layers is in a range of from 20 to 1,000 nm.

16. An inspection method as set forth in claim 15, wherein said metal layer has a thickness of 10 to 100 nm.

17. An inspection method as set forth in claim 15, wherein said metal layer is made of Be, Mg, or Al.

18. An inspection method as set forth in claim 15, wherein said metal layer is not located on a side of the first surface of said film.

19. An inspection method as set forth in claim 11 or 12, wherein said primary beam is an electron beam or a charged-particle beam, and wherein said secondary signal is at least any one type of backscattered electrons, secondary electrons, absorption current, cathodoluminescent light, and X-rays.

* * * * *

UNITED STATES PATENT AND TRADEMARK OFFICE
CERTIFICATE OF CORRECTION

PATENT NO. : 7,968,843 B2
APPLICATION NO. : 12/349195
DATED : June 28, 2011
INVENTOR(S) : Hidetoshi Nishiyama It is certified that error appears in the above-identified patent and that said Letters Patent is hereby corrected as shown below:

Column 14, Line 29, Claim 4, "claim 1," should read -- claim 1 or 3, --

Signed and Sealed this
First Day of November, 2011

David J. Kappos
*Director of the United States Patent and Trademark Office*